US008782780B2

(12) United States Patent
Friedlander et al.

(10) Patent No.: US 8,782,780 B2
(45) Date of Patent: Jul. 15, 2014

(54) HIERARCHICAL ORGANIZATION OF DATA ASSOCIATED WITH EVENTS

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 1197 days.

(21) Appl. No.: 11/227,393

(22) Filed: Sep. 15, 2005

(65) Prior Publication Data

US 2006/0070127 A1   Mar. 30, 2006

Related U.S. Application Data

(63) Continuation-in-part of application No. 10/952,016, filed on Sep. 28, 2004, now Pat. No. 8,131,472.

(51) Int. Cl.
| | | |
|---|---|---|
| *G06F 11/00* | (2006.01) | |
| *G06F 12/14* | (2006.01) | |
| *G06F 12/16* | (2006.01) | |
| *G08B 23/00* | (2006.01) | |
| *G06F 7/00* | (2006.01) | |
| *G06F 17/30* | (2006.01) | |
| *G06Q 50/26* | (2012.01) | |

(52) U.S. Cl.
CPC .... *G06F 17/30589* (2013.01); *G06F 17/30522* (2013.01); *G06Q 50/26* (2013.01)
USPC ............................................. 726/22; 707/778

(58) Field of Classification Search
CPC .................. G06F 17/30589; G06F 17/30386; G06F 17/30424; G06F 17/30522; G06F 17/30554; G06Q 50/26; G06Q 50/265
USPC .................................. 707/769, 778, 783, 829
See application file for complete search history.

(56) References Cited

U.S. PATENT DOCUMENTS

| | | | |
|---|---|---|---|
| 4,328,978 A | 5/1982 | McLaughlin | |
| 5,692,501 A | 12/1997 | Minturn | |
| 6,058,391 A | 5/2000 | Gardner | |
| 6,173,284 B1 * | 1/2001 | Brown | ........................... 707/702 |
| 6,189,004 B1 | 2/2001 | Rassen et al. | |

(Continued)

FOREIGN PATENT DOCUMENTS

| | | |
|---|---|---|
| JP | 2002312373 | 4/2001 |
| JP | 2002342484 | 2/2002 |
| WO | WO 01/08077 A1 | 2/2001 |

OTHER PUBLICATIONS

Adam et al., "Positive Patient Identification: a Practical Solution to a Challenging Problem," Toward an Electronic Patient '97. Conference and Exposition. Proceedings, Pt. vol. 3, pp. 100-108, 1997.

(Continued)

*Primary Examiner* — Philip Chea
*Assistant Examiner* — Trong Nguyen
(74) *Attorney, Agent, or Firm* — Yudell Isidore Ng Russell PLLC

(57) ABSTRACT

Methods, data structures, systems and computer program products are provided for organizing security data. A triggering security event is hierarchically related to at least one additional security event based on a possible relationship between the triggering security event and the at least one additional security event in a computer database environment.

14 Claims, 5 Drawing Sheets

(56) References Cited

U.S. PATENT DOCUMENTS

| | | | |
|---|---|---|---|
| 6,385,604 | B1 | 5/2002 | Bakalash et al. |
| 6,405,213 | B1* | 6/2002 | Layson et al. ............... 707/758 |
| 6,509,898 | B2 | 1/2003 | Chi et al. |
| 6,578,043 | B2 | 6/2003 | Nye |
| 6,629,106 | B1 | 9/2003 | Narayanaswamy et al. |
| 2002/0059183 | A1 | 5/2002 | Chen |
| 2002/0099691 | A1 | 7/2002 | Lore et al. |
| 2002/0099692 | A1 | 7/2002 | Shah et al. |
| 2002/0156791 | A1 | 10/2002 | Nesamoney et al. |
| 2002/0184225 | A1 | 12/2002 | Ghukasyan |
| 2003/0074222 | A1 | 4/2003 | Rosow et al. |
| 2003/0088438 | A1 | 5/2003 | Maughan et al. |
| 2003/0126148 | A1 | 7/2003 | Gropper et al. |
| 2003/0177132 | A1 | 9/2003 | Thomas et al. |
| 2003/0191669 | A1 | 10/2003 | Fitzgerald et al. |
| 2003/0195898 | A1 | 10/2003 | Agarwal et al. |
| 2004/0006532 | A1* | 1/2004 | Lawrence et al. ............... 705/38 |
| 2004/0193572 | A1* | 9/2004 | Leary ................... 707/1 |
| 2005/0102210 | A1* | 5/2005 | Song et al. ............... 705/35 |

OTHER PUBLICATIONS

Chatfield, "Marketing an HMO by 'Smart' ID Cards with Patient History on an Electronic Medical Record," Proceedings. Toward an Electronic Patient Record '96. Twelfth International Symposium on the Creation of Electronic Health Record System and Global Conference on Patient Cards, Pt. vol. 1, pp. 608-620, 1996.

Gabrieli, "Guide for Unique Healthcare Identifier Model," *Journal of Clinical Computing*, vol. 21, No. 5, pp. 101-139, 1993.

Goehring, "Identification of Patients in Medical Databases—Soundex Codes Versus Match Code," *Medical Informatics*, vol. 10, No. 1, pp. 27-34, Jan.-Mar. 1985.

Goodwin et al., "Data Mining for Preterm Birth Prediction," pp. 46-51.

Grimson et al., "The SI Challenge in Health Care," *Communications of the ACM*, vol. 43, No. 6, Jun. 2000, pp. 49-55.

Hoshiai et al., "SION Architecture: Semantic Information-Oriented Network Architecture," *Transactions of the Institute of Electronics, Information and Communication Engineers B.*, vol. J84-B, No. 3, pp. 411-424, Mar. 2001.

Lowery et al., "Barriers to Implementing Simulation in Health Care," Proceedings from the 1994 Winter Simulation Conference, pp. 868-875.

Polak et al., "Using Automated Analysis of the Resting Twelve-Lead ECG to Identify Patients at Risk of Developing Transient Myocardial Ischaemia—an Application of an Adaptive Logic Network," *Physiological Measurement*, vol. 18, No. 4, pp. 317-325, Nov. 1997.

Shelfer et al., "Smart Card Evolution," *Communications of the ACM*, vol. 45, No. 7, Jul. 2002, pp. 83-88.

Wang, C., "A COBRA-based Object Framework with Patient Identification Translation and Dynamic Linking. Methods for Exchanging Patient Data," *Methods of Information in Medicine*, vol. 38, No. 1, pp. 56-65, Mar. 1999.

Zarowski et al., "Some Algorithms for Circadian Rhythm Identification," 2001 IEEE Pacific Rim Conference on Communications, Computers, and Signal Processing, Pt. vol. 2, pp. 425-428, 2001.

\* cited by examiner

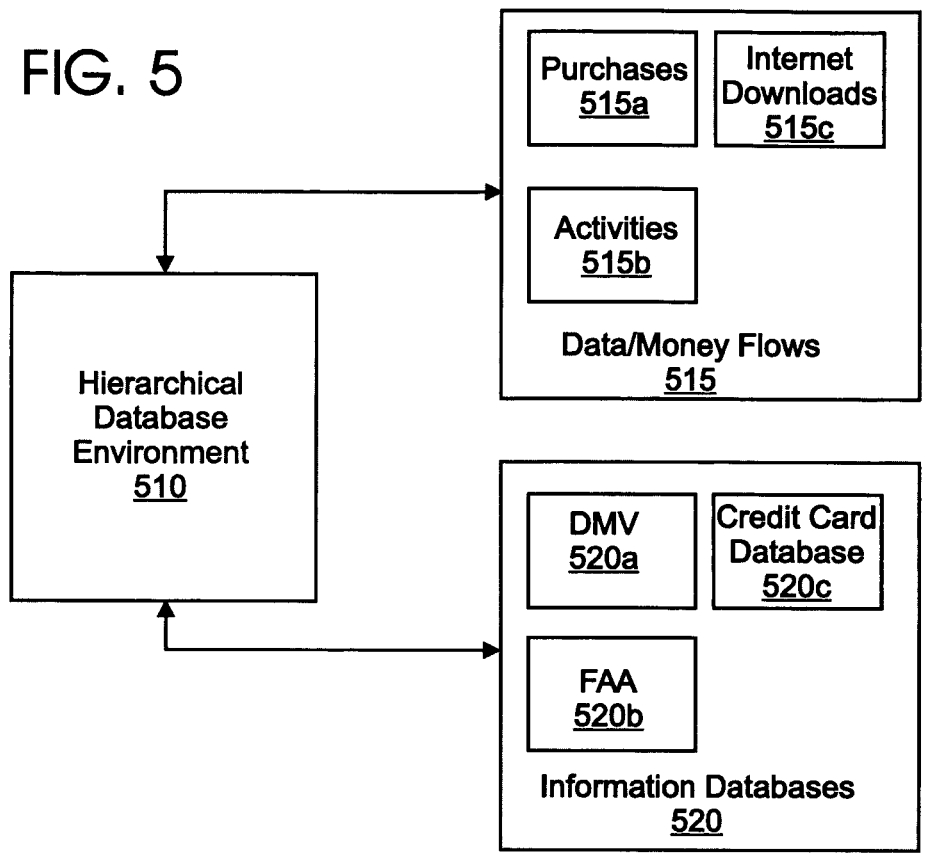
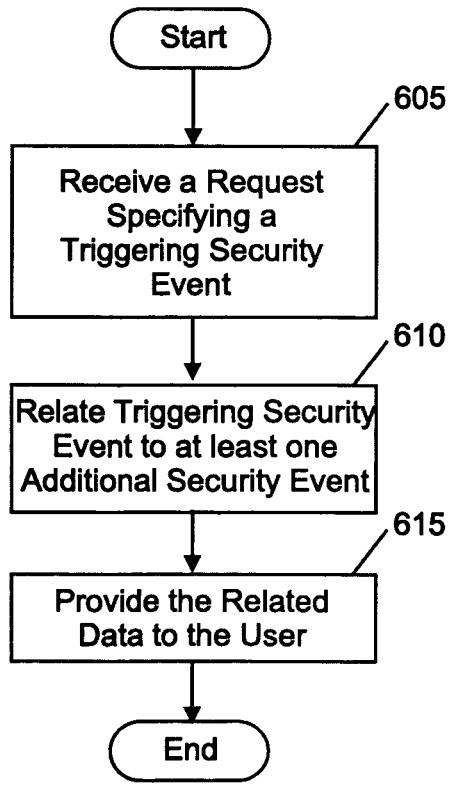

HIERARCHICAL ORGANIZATION OF DATA ASSOCIATED WITH EVENTS

CLAIM OF PRIORITY

This application is a continuation in part of and claims priority from co-pending U.S. patent application Ser. No. 10/952,016 filed Sep. 28, 2004, the content of which is hereby incorporated herein by reference as if set forth in its entirety.

FIELD OF THE INVENTION

The invention relates to data processing in general and, more particularly, to organization of data.

BACKGROUND OF THE INVENTION

As the threat of terrorism increases, the need to identify suspicious activities is very important. However, the identification of these activities can be very difficult. For example, the purchase of fertilizer does not on its face appear suspicious, but this fertilizer could be used to build a bomb. Thus, it is difficult to identify data of interest in criminal and homeland security investigations because each of the pieces by themselves may appear innocuous, but when the pieces are all put together they may reveal a terrorist plot.

For example, in the recent London attacks a large amount of pure hydrogen peroxide, a large industrial refrigerator and heat tags were purchased. Each of these purchases might be slightly suspicious, or not all, by themselves, but together, if known, may set off flags as being highly suspicious as all of the things that were purchased were purchased within a defined location in close time proximity. This information, even if entered into a database environment, may not stand out as suspicious because this information is difficult to analyze and the recognition of a pattern that would set off a flag may require both experience and intuition, which a computer database does not typically have. One example of an existing criminal database is International Business Machine's Criminal Information Warehouse (CIW). CIW is a large scale database which includes information on criminals, potential criminals, persons of interest and the like.

SUMMARY OF THE INVENTION

Some embodiments of the present invention provide methods, data structures, systems and computer program products for organizing security data. A triggering security event is hierarchically related to at least one additional security event based on a possible relationship between the triggering security event and the at least one additional security event in a computer database environment.

In further embodiments of the present invention, a request specifying the triggering security event may be received at the computer database environment. The at least one additional security event possibly associated with the specified triggering security event may be provided responsive to the request.

In still further embodiments of the present invention, a likelihood that the triggering security event and the at least one additional security event are related exceeds a predetermined threshold may be determined. An alert indicating that the predetermined threshold has been exceeded may be generated if it is determined that the predetermined threshold has been exceeded.

In some embodiments of the present invention, the at least one additional security event may include security events occurring at different times within a specified time period and/or a specified location. The triggering security event may be identified based on at least one identified pattern defining security events. The identified patterns may be fine tuned and/or identified patterns may be added to the computer database environment based on the triggering security event and/or the at least one additional security event. The identified patterns may be automatically fine tuned and/or added based on normal patterns, the normal patterns including season of the year, holidays, climatic norms and abnormalities and/or events of national and international significance. The at least one identified pattern may be identified based on purchases made, actions taken, data flows and/or money flows.

In further embodiments of the present invention, the possible relationship between the triggering security event and the at least one additional security event comprises a relationship between people associated with the triggering security event and the at least one additional security event.

BRIEF DESCRIPTION OF THE DRAWINGS

FIG. 5 is a block diagram illustrating operations of systems according to some embodiments of the invention.

FIGS. 6 and 7 are flowcharts illustrating operations according to various embodiments of the present invention.

DETAILED DESCRIPTION OF EMBODIMENTS OF THE INVENTION

Figure 1:
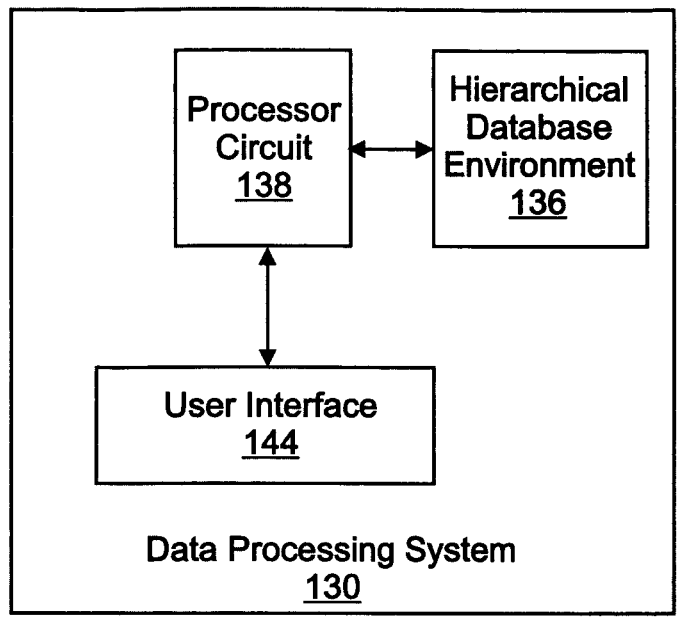
FIG. 1 is a block diagram illustrating systems according to some embodiments of the invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of skill in the art, the invention may be embodied as a method, data structure, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable storage medium may be utilized including hard disks, CD-ROMs, optical storage devices, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to a flowchart illustration and/or block diagrams of methods, systems, computer program products and data structures according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to FIGS. 1 through 7. As described herein, some embodiments of the present invention provide a database environment for storing security data. A triggering security event may be identified in the database environment. As used herein a "triggering event" refers to any event, for example, a purchase, an internet download, a training course or other activity, that may appear suspicious. For example, a triggering security event may be, for example, the purchase of a large amount of fertilizer or downloading maps of places if interest, for example, New York City or Washington D.C. Once this triggering security event is identified in the database environment, one or more additional security events that may be related to the triggering security event may be identified. As used herein, "additional security events" refer to any event that may appear suspicious and may possibly be related to the triggering security event. The additional security events may have occurred within a predetermined time period of the triggering security event, for example, thirty days before or after the triggering security event, and/or within a predetermined distance of the location of the triggering security event, for example, within a thirty mile radius. Relationships between the triggering security event and the additional security events may be identified. For example, each of the events may be associated with people who all attend the same church. Once this relationship has been established, an alert indicating that a predetermined threshold, i.e., the relationship, has been met may be generated. The threshold may be customized by the user. At this point a person, for example, law enforcement or homeland security personnel, may look at these events more closely and an investigation may be opened. Thus, according to some embodiments of the present invention, first degree relationships may be established between a plurality of events that may themselves seem unrelated. Furthermore, once these first degree relationships are established, the seemingly innocent individual events convey a different story as discussed further herein below.

Referring now to FIG. 1, a block diagram illustrating systems, for example, data processing system 130, according to some embodiments of the invention will be discussed. In particular, a hierarchical database environment 136 operates under the control of a processor circuit 138. The processor circuit 138 can be a general purpose processor circuit within a general purpose or application specific computer. As described above, the processor circuit 138 may use elements of both hardware and software to carry out the functions described herein.

The system 130 also includes a user interface 144. The user interface device 144 may include, for example, a keyboard or keypad, a display, microphone, speaker and/or other types of input/output functionality that may enable the user to interact with the hierarchical database environment 136 via the processor circuit 138. It will be understood that the elements shown in FIG. 1 may operate on a single computer system or may be distributed among two or more computer systems that operate in cooperation with one another to carry out the operations described herein. The two or more computers may communicate with one another over a network, such as a local area network.

The hierarchical database environment 136 is configured to store security data. The security data may be collected from databases, such as the department of motor vehicles (DMV) database, the FAA database, credit card company databases and the like. Within this security data, triggering security events may be identified. Furthermore, one or more additional security events may be identified based on a possible relationship between the triggering security event and the one or more additional events. For example, the relationship may indicate that all of the events are associated with people who attend the same church.

Thus, for example, the triggering security event may be the purchase large industrial refrigerator by a person who does not typically have the need for such an appliance. According to some embodiments of the present invention, the processor 138 may be configured to search the hierarchical database environment 136 for additional events that may possibly be related to the triggering security event. For example, someone living in the same apartment building of the person who bought the refrigerator may have purchased a large amount of pure hydrogen peroxide. This event may be identified as an additional security event associated with the triggering security event. The processor 138 may be configured to search the database 136 for events in a specified time period and/or location. For example, the database may be configured to search for events thirty days before and/or after the triggering security event in a thirty mile radius around the location of the triggering security event. It will be understood that these time periods and distances are provided for exemplary purposes only and that embodiments of the present invention are not limited to this configuration. For example, the search area and time period may be user customizable, as different organizations have different needs. For example, if the database 136 was being used by a local police department, the distance specification may be much more limited than if the database 136 was being used by the Federal Bureau of Investigation (FBI). The triggering security event and the additional security events, referred to collectively as security events) may be stored separately in a memory of the hierarchical database environment 136.

In some embodiments of the present invention, a user, for example, homeland security personnel, may access the hierarchical database environment 136 to request security data associated with a triggering security event. Because the triggering security event is hierarchically related to possibly related additional security events, the hierarchical database environment 136 can provide the security data for user access in a more convenient fashion.

In certain embodiments of the present invention, the security data stored in the hierarchical database environment 136 may be searched and analyzed using conventional data mining tools, such as iMiner, SAS miner and the like. Thus, these data mining tools may be used to identify patterns in the security data stored in the database, which may possibly be useful in identifying a suspicious situation that may possibly lead to, for example, a terrorist attack. For example, the database may include a list of chemicals that are commonly used in bomb making. If one of these chemicals is purchased in bulk, the database 136 may be configured to search for the purchase of one or more other items/chemicals that are also used in bomb making within a certain location and time period of the first purchase. These patterns may be changed over time, for example, new chemicals, when discovered, may be added over time.

In some embodiments of the present invention, the patterns may be changed manually by a user, for example, homeland security personnel. The patterns may be adjusted for perturbations, such as season of the year, holidays, climatic norms and abnormalities, events of national and international significance (elections, state funerals, etc.) and the like. It will be understood that the adjustments to the patterns may be performed automatically by systems according to some embodiments of the present invention. Furthermore, systems according to some embodiments of the present invention may be configured to discover and/or remember normal patterns including adjustments for perturbations, such as season of the year, holidays, climatic norms and abnormalities, events of national and international significance (elections, state funerals, etc.) and the like without departing from the scope of the present invention.

In certain embodiments of the present invention, security data may be retrieved using query tools, such as SQL, MicroStrategy, BusinessObject, Cognos and the like. Furthermore, some embodiments of the present invention may be used in combination with existing database software, such as DB2 from International Business Machines, Armonk, N.Y., the assignee of the present application. Other database software that may be used in some embodiments of the present invention includes Oracle from Oracle of Redwood Shores, Calif., SQL Server from Microsoft Corporation of Redmond, Wash. and Sysbase from Sysbase of Dublin, Calif. The exemplary database software provided herein is provided for exemplary purposes only and embodiments of the present invention are not limited to these examples.

In some embodiments according to the invention, the security events are stored in the hierarchical database environment 136 in data structures that are hierarchically linked. For example, security data related to different people can be hierarchically related to one another because the people who are associated with the security events are somehow related, for example, the people all attend the same church. Some embodiments of the present invention may be included in a CIW product offered by IBM of Armonk, N.Y.

Figure 2:
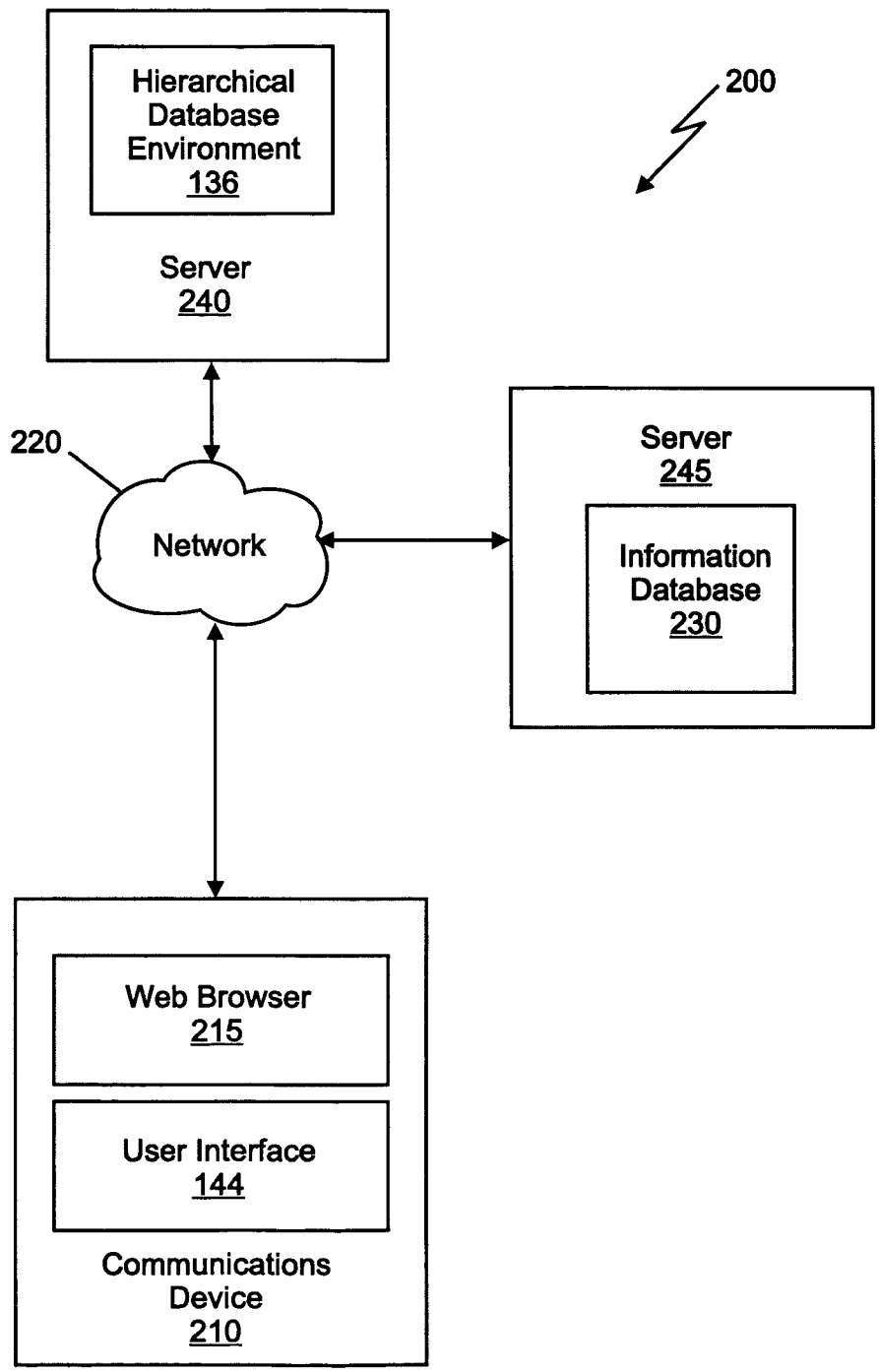
FIG. 2 is a block diagram illustrating some embodiments of the present invention in an exemplary network environment.

Methods of collecting and storing data in databases are known to those having skill in the art and, therefore, will not be discussed in detail herein. An exemplary method of collecting and storing data in databases will be discussed with respect to FIG. 2. A block diagram illustrating an exemplary environment for security data according to some embodiments of the present invention is illustrated in FIG. 2. As illustrated, the environment 200 may include a communications device 210, a network 220 and first and second servers 240 and 245. The communications device 210 may be, for example, a laptop computer, a desktop computer, a personal data assistant (PDA), a web capable mobile terminal or any device capable of communicating with the network 220. The communications device 210 may communicate over the network 220, for example, the internet, through a telephone line, a digital subscriber link (DSL), a broadband cable link, a wireless link or the like. The first and second servers 240 and 245 may also communicate over the network 220. Thus, the network 220 may convey data between the communications device 210 and the first and second servers 240 and 245.

As further illustrated, the communications device may include a web browser 215 that may be accessed through the user interface 144. The web browser 215 may allow, for example, a criminalist, FBI agent, homeland security personnel or the like access to a text or graphical interface used to enter information related to a triggering security event. For example, the web browser may include a graphical interface that requests such information as a name of a person or persons associated with the triggering security event, their address, phone number and the like, the type of event, for example, a purchase or a download and the date and time of the event. Furthermore, as the security data is collected, for example, purchases by persons of interest, it may be entered using the graphical user interface on the web browser 215. As used herein, a "person of interest" refers to any person, for example, a criminal or potential criminal, that may arouse suspicion for any reason. Once an security data is entered into the graphical user interface, the user may indicate that the security data be stored in the hierarchal database environment 136 by, for example, pressing an enter key on a keypad. The web browser 215 may communicate the security data over the network 220 to the first server 240, which may then store the security data in the hierarchal database environment 136 on the first server 240.

It will be understood that although security data may be stored in the database 136 by a user of the computing device 210 as discussed above, embodiments of the present invention are not limited to this configuration. For example, the database 136 may be configured to watch external databases, for example, the DMV database, credit card databases, the FAA databases, for suspicious activity or activity by persons of interest, which may be automatically stored in the database 136 without departing from the scope of the present invention as will be discussed further below.

Furthermore, a user, for example, an FBI agent, may also use the web browser 215 to search and analyze the security data stored in the hierarchal database environment 136. As illustrated in FIG. 2, the second server 245 may include information databases 230 including, for example, credit card databases, DMV databases, hospital databases, data flows and money flows (bank databases). In some embodiments of the present invention, the information databases 230 may include and/or have access to text based evidence. For example, the FBI agent may extract discrete and/or syntactical semantic data from the text based sources. The FBI agent may use these information databases 230 to obtain information about additional security events that could be possibly related to the triggering security event as discussed further below. The information in the information databases 230 may provide further support that a flagged security event indicated a possible problem that may lead to, for example, a terrorist attack. It will be understood that the environment 200 provided in FIG. 2 is provided for exemplary purposes only and that embodiments of the present invention are not limited to this configuration.

Furthermore, methods, systems and computer program products according to some embodiments of the present invention may be capable of providing security events and/or information from the hierarchical database 136 and/or the external databases, for example, information databases 230, based on the who the user is, i.e. what group does the user belong to and what is his/her role/title. For example, if the user is a police officer, the security events/information provided may include, but is not limited to, information provided in a daily police report. Other text based evidence that may be searched and provided according to some embodiments of the present invention may include, but is not limited to, tickets, coast guard duty reports, harbor master reports, airport manager reports, harbor schedules, train schedules, bus schedules, container landing schedules, plane schedules, hazardous materials shipment manifests and the like. In some embodiments of the present invention, these text based evidence databases may be searched without being designated to be searched, i.e. searched automatically without user intervention. These text based evidence databases may also be designated to be searched without departing from the scope of the present invention.

Figure 3:
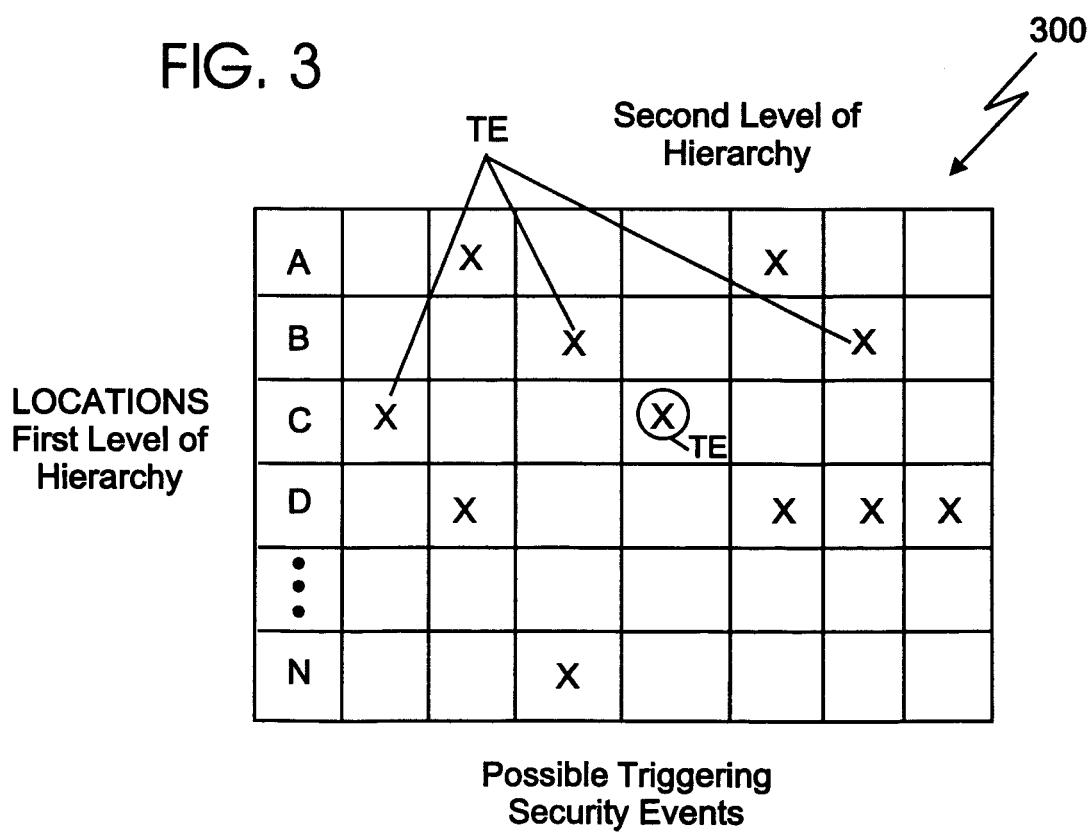
FIG. 3 is a schematic illustration of hierarchical relationships between a triggering security event and at least one additional security event in a database environment according to some embodiments of the invention.

Referring now to FIG. 3, a schematic representation of security stored in a hierarchical database environment 136 according to some embodiments of the invention will be discussed. Table 300 in FIG. 3 illustrates an unstructured arrangement of security data occurring at locations A through N for the purpose of illustrating the hierarchical relationship of the data stored therein to the triggering security event (TE) according to some embodiments of the invention. As used herein, "unstructured" security data refers to data that does not necessarily logically fit together well at first glance, i.e., data that may be seemingly innocuous. It will therefore be understood that the unstructured security data in table 300 is used to describe the hierarchical relationship between the security data stored therein and the triggering security event.

It will be understood that each of the Xs in Table 300 represents security data for different locations A through N either entered by a user or obtained from one or more external databases, for example, the DMV database. This illustrates a first level of hierarchy. For example, the "X's" may correspond to specific security events that occurred in the indicated location within a particular time period. For example, two security events may have occurred in location A in the particular time period. As illustrated, a triggering security event (TE) may be identified in the database environment in location C. Once this triggering security event (TE) is identified, the user may specify a specific location and/or time period to be searched for additional security events that may be possibly related to the triggering security event. As illustrated in FIG. 3, two events in location B and one event in location C have been identified as additional security events that may possibly be related to the triggering security event (TE). This illustrates a second level of hierarchy in the database.

Figure 4A:
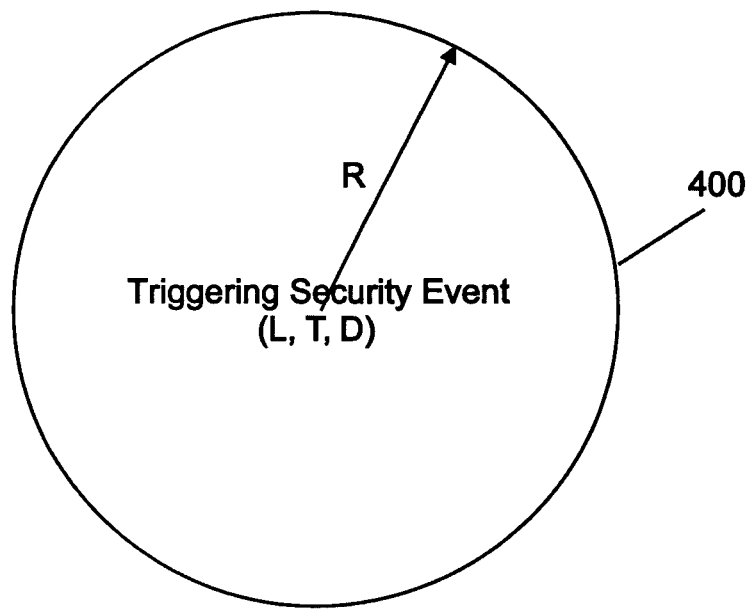
FIG. 4A is diagram illustrating a location of a triggering event and the possible predefined location for additional security events according to some embodiments of the present invention.

Referring now to FIG. 4A, a diagram illustrating a search region according to some embodiments of the present invention will be discussed. As discussed above, a triggering security event may be identified using a database according to some embodiments of the present invention. The triggering security event may have an associated location, time and date (L, T, D). Thus, a search region 400 may be identified based on the location of the triggering security event. For example, if the triggering security event occurred in London, the search region 400 may be identified by a thirty mile radius R around London (the location of the triggering security event). As discussed above, the size of the search region 400 may be customized by the user. Thus, if the user is a local police department, the search region 400 may be much smaller than if the user is the FBI. The FBI's search region could be, for example, the entire United States.

Figure 4B:
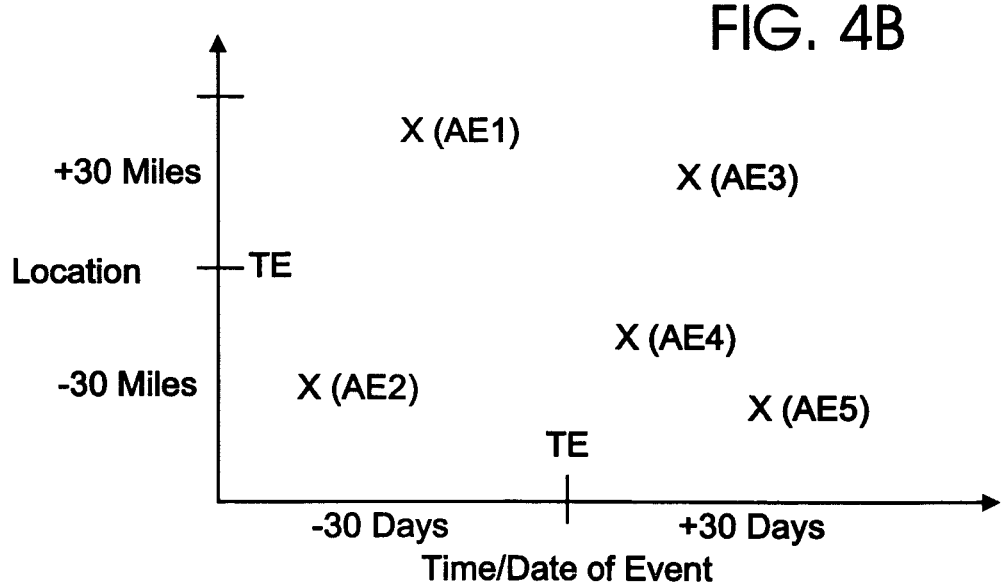
FIG. 4B is a graph of location vs. time illustrating the location and time of the triggering event and possible additional security events according to some embodiments of the present.

Referring now to FIG. 4B, a graph that illustrates location versus time of the triggering security event and additional security events according to some embodiments of the present invention will be discussed. Similar to the search region 400, the time period of the search may be set based on the date and time of the triggering security event. For example, as shown in FIG. 4B, the time period for the search may be thirty days before and/or after the occurrence of the triggering security event. As discussed above, this time period may be customizable by the user and may vary greatly depending on the user's objective. As further illustrated in FIG. 4B, the security data may be collected at different times and locations. According to some embodiments of the present invention, these additional security events (AE1 to AE5) may be identified as possibly related to the triggering security event (TE), which may otherwise be difficult to access in an unstructured database.

Referring now to FIG. 5, a block diagram that illustrates operations of hierarchical database environments according to some embodiments of the invention will be discussed. In particular, a database environment 510 according to some embodiments of the invention can operate as described above and may access data/money flows 515, as well as information databases 520.

In operation, a user, for example, homeland security personnel, may operate the hierarchical database environment 510 to identify security data associated with a triggering security event to investigate potential relationships among the data for the purposes of, for example, thwarting a terrorist attack. In some embodiments of the present invention, the user may operate the hierarchical database environment 510 to access additional security events associated with the triggering security event. By accessing the security data in this way, the data may be viewed in a more hierarchical fashion, thereby enabling the user to further investigate a potential relationship, for example, between a purchase of a refrigerator and a purchase of hydrogen peroxide by accessing the DMV database 520a included among the information databases 520. In other words, the DMV database may be used to provide information with respect to the person or persons who made these purchases. For example, the DMV database may reveal that these persons live in the same apartment building.

If the data in the DMV database 520a indicates a relationship between the persons who made the purchases, the user may further access other information related to these individuals, for example, data/money flows 515 associated with these individuals. For example, the data flows may include current internet downloads 515c made by one or more of these individuals. For example, one of these individuals, for example, the person who bought the large quantity of hydrogen peroxide, may have also downloaded a map of London's subway system from the Internet. This may be useful in identifying a possible terrorist attack on London.

It will be understood that the information databases 520 can include further sources, such as an FAA database 520b, credit card database 520c and any other informational database that may include useful information. It will be further understood that the data/money flows 515 can further include purchases 515a, activities 515b and any data or money transaction made by, for example, a person of interest, that may be of interest to the user. The data/money flows 515 and the information databases 520 provided in FIG. 5 are provided for exemplary purposes only and, thus, embodiments of the present invention are not limited to the content thereof. It will also be understood that some of these databases contain private information which may only be accessed by those having clearance to do so. For example, the police, the FBI, the CIA and the like may have a warrant. Thus, according to some embodiments of the present invention users may be able to establish relationships among this seemingly unrelated security data to possibly thwart a terrorist attack or at least identify people or groups thereof who are up to no good.

Figure 7:
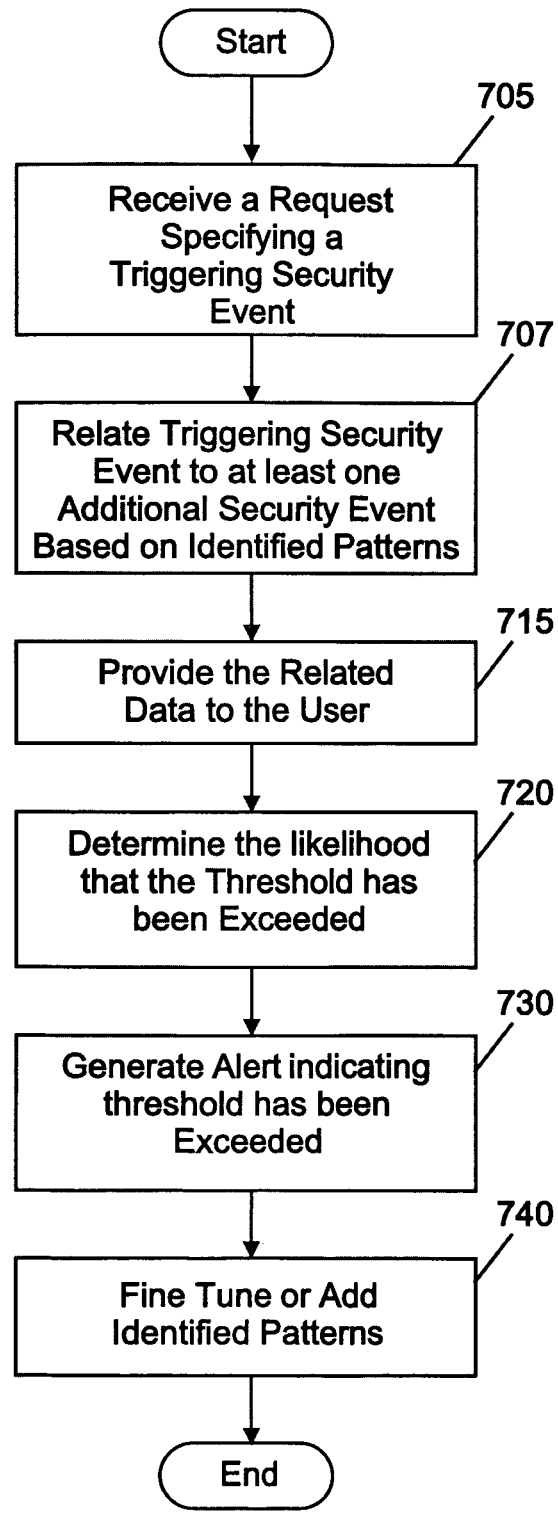

Referring now to FIGS. 6 and 7, flowcharts illustrating operations of hierarchical database environments according to various embodiments of the present invention will now be discussed. In some embodiments according to the invention, a request that specifies a triggering security event is provided to the hierarchical database environment (block 605). As described above, the triggering security event may identify any suspicious activity that may or may not be associated with a person of interest. For example, in some embodiments according to the invention, the triggering security event may be multiple foreign persons signed up to attend flight school.

The hierarchical database environment can be used to locate and identify additional security events that may be related to the triggering security events (block 610). The additional security events may be removed from the triggering security event in both time and location. These may be set as parameters of the search. In some embodiments of the present invention, the possible relationship between the triggering security event and the at least one additional security event may be a relationship between people associated with the triggering security event and the at least one additional security event. For example, in some embodiments according to the invention, the database may be used to determine that the same people signed up for flight school also accessed the flight plans of major airlines flying out of major cities and purchases large amounts of jet fuel. As discussed above, the additional security events may be identified in the database using conventional data mining techniques. Thus, the related security events may be provided to the user in a format that can be analyzed to possibly thwart a terrorist threat (block 615).

Referring now to FIG. 7, a request that specifies a triggering security event is provided to the hierarchical database environment (block 705). The hierarchical database environment can be used to locate and identify additional security events that may be related to the triggering security events based on identified patterns and rules (block 707). The related security event may be provided to the user in a format that can be analyzed to possibly thwart a terrorist threat (block 715). A likelihood that the triggering security event and the at least one additional security event are related exceeds a predetermined threshold may be determined (block 720). For example, if the triggering security event and the additional security events were performed by people who live in the same apartment building, this may cause the threshold to be exceeded because an adequate relationship between the events has been established. An alert may be generated indicating that the predetermined threshold has been exceeded if it is determined that the predetermined threshold has been exceeded (block 730). Thus, once the security events reach an alert level, law enforcement personnel may be alerted about the identified security events. The law enforcement personnel may then look into the situation and take action if necessary.

In some embodiments of the present invention, the patterns and/or rules may be fine tuned based on the triggering security event and/or the at least one additional security event (block 740). In other words, the database environment may learn and add patterns as different ones are identified. The patterns may be identified based on, for example, purchases made, actions taken, data flows and/or money flows.

It will be understood that the circuits and other means supported by each block and combinations of blocks can be implemented by special purpose hardware, software or firmware operating on special or general purpose data processors, or combinations thereof. It should also be noted that, in some alternative implementations, the operations noted in the blocks may occur out of the order noted in the figures. For example, two blocks shown in succession may, in fact, be executed substantially concurrently, or the blocks may sometimes be executed in the reverse order.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A method of organizing security data, comprising:
   hierarchically relating a triggering security event at a first level of hierarchy with one or more additional security events at a second level of the hierarchy that is lower than the first level of the hierarchy based on a possible relationship between the triggering security event and the one or more additional security events in a computer database environment maintained in a computer readable storage medium and associated with a data processing system;

receiving, via the data processing system, a request from a user specifying the triggering security event at the computer database environment;

identifying, via the data processing system, a search region based on a location associated with the specified triggering security event and a search time period based on a date and time of the specified triggering security event, wherein the search time period and a size of the search region are customized by the user; and providing, from the computer database environment, the one or more additional security events possibly associated with the specified triggering security event based on the identified search region and search time period responsive to the request, wherein the providing the one or more additional security events is based on a group of the user and role or title of the user.

2. The method of claim 1, further comprising:

determining a likelihood that the specified triggering security event and the one or more additional security events, present in the computer database environment, are related exceeds a predetermined threshold; and generating an alert indicating that the predetermined threshold has been exceeded when the predetermined threshold has been exceeded.

3. The method of claim 2, wherein the one or more additional security events comprise multiple security events each occurring at different times within a specified time period and/or a specified location.

4. The method of claim 2, further comprising identifying the triggering security event based on one or more first identified patterns defining security events.

5. The method of claim 4, further comprising fine tuning the one or more first identified patterns and/or adding one or more second identified patterns to the computer database environment based on the triggering security event and/or the one or more additional security events.

6. The method of claim 5, further comprising automatically fine tuning the one or more first identified patterns and/or adding the one or more second identified patterns based on normal patterns, the normal patterns including season of the year, holidays, climatic norms and abnormalities and/or events of national and international significance.

7. The method of claim 4, wherein the one or more first identified patterns are identified based on purchases made, actions taken, data flows and/or money flows.

8. A data processing system for organizing security data comprising:

a computer database environment maintained in a computer readable storage medium and configured to store a triggering security event object at a first level of hierarchy and one or more additional security event objects at a second level of the hierarchy that is lower than the first level of the hierarchy, wherein the one or more additional security event objects are identified based on a possible relationship between the triggering security event object and the one or more additional security event objects; and a processor circuit configured to hierarchically relate the triggering security event object to the one or more additional security event objects in the computer database environment, receive a request from a user specifying the triggering security event object at the computer database environment, identify a search region based on a location associated with the specified triggering security event object and a search time period based on a date and time of the specified triggering security event object, wherein the search time period and a size of the search region are customized by the user, and provide the one or more additional security event objects possibly associated with the specified triggering security event object based on the identified search region and search time period responsive to the request, wherein the providing the one or more additional security event objects is based on a group of the user and role or title of the user.

9. The system of claim 8, wherein the processor circuit is further configured to determine a likelihood that the specified triggering security event object and the one or more additional security event objects are related exceeds a predetermined threshold and generate an alert indicating that the predetermined threshold has been exceeded when the predetermined threshold has been exceeded.

10. The system of claim 8, wherein the one or more additional security event objects comprise data associated with multiple security events each occurring at different times within a specified time period and/or a specified location.

11. The system of claim 8, wherein the processor circuit is further configured to identify the triggering security event object based on one or more first identified patterns defining security events.

12. The system of claim 11, wherein the processor circuit is further configured to fine tune the one or more first identified patterns and/or add one or more second identified patterns to the database environment based on the triggering security event object and/or the one or more additional security event objects.

13. The system of claim 11, wherein the one or more first identified patterns are identified based on purchases made, actions taken, data flows and/or money flows.

14. The system of claim 8, wherein a possible relationship between the triggering security event object and the one or more additional security event objects comprises a relationship between people associated with the triggering security event object and the one or more additional security event objects.

* * * * *